(12) United States Patent
Tarassenko et al.

(10) Patent No.: US 8,949,072 B2
(45) Date of Patent: Feb. 3, 2015

(54) NOVELTY DETECTION WITH MISSING PARAMETERS

(75) Inventors: Lionel Tarassenko, Oxford (GB); Alistair Hann, Oxford (GB)

(73) Assignee: Oxford Biosignals Limited, Thame (GB)

( * ) Notice: Subject to any disclaimer, the term of this patent is extended or adjusted under 35 U.S.C. 154(b) by 962 days.

(21) Appl. No.: 13/122,801

(22) PCT Filed: Oct. 9, 2009

(86) PCT No.: PCT/GB2009/002408
§ 371 (c)(1),
(2), (4) Date: Jul. 5, 2011

(87) PCT Pub. No.: WO2010/041019
PCT Pub. Date: Apr. 15, 2010

(65) Prior Publication Data
US 2011/0265026 A1    Oct. 27, 2011

(30) Foreign Application Priority Data
Oct. 9, 2008 (GB) .................................. 0818544.9

(51) Int. Cl.
*G06F 3/048* (2013.01)
*G06K 9/62* (2006.01)
(Continued)

(52) U.S. Cl.
CPC .......... *G06K 9/6284* (2013.01); *A61B 5/02055* (2013.01); *A61B 5/6843* (2013.01);
(Continued)

(58) Field of Classification Search
CPC .. A61B 5/02055; A61B 5/021; A61B 5/0816; A61B 2560/0276; A61B 5/6843; A61B 5/0245; A61B 5/145; G06F 19/3443; G06F 19/36; G06K 9/00536; G06K 9/6284
USPC .............. 702/19, 67, 181, 189; 600/301, 484, 600/512, 544
See application file for complete search history.

(56) References Cited

U.S. PATENT DOCUMENTS 7,031,857 B2 *  4/2006  Tarassenko et al. ............ 702/67
7,373,198 B2 *  5/2008  Bibian et al. .................. 600/544

(Continued)

FOREIGN PATENT DOCUMENTS

WO    WO-02/03041 A1    1/2002
WO    WO-02/096282 A2   12/2002

*Primary Examiner* — Carol S Tsai
(74) *Attorney, Agent, or Firm* — Harness, Dickey & Pierce, P.L.C.

(57) ABSTRACT

A method of obtaining a consistent evaluation of the state of the system which has been monitored by measurement of multiple parameters of that system. The multiple parameters are used to calculate a single dimensional value based on the distance between the current state and normal states of the system using a Parzen Windows probability function. Consistent single dimensional values regardless of the dimensionality of the original data set can be obtained by finding a relationship between the single dimensional value and the probability of status of the system. Different relationships are obtained for different dimensionalities of data sets. Sensor malfunction can also be detected by testing the probability of the state implied by measuring all of the available parameters against the probability of the state implied by ignoring different individual ones of the parameters. A significant disparity in the two probabilities indicate possible sensor malfunction.

30 Claims, 6 Drawing Sheets

(51) Int. Cl.
   *A61B 5/0205* (2006.01)
   *A61B 5/00* (2006.01)
   *G06F 19/00* (2011.01)
   *G06K 9/00* (2006.01)
   *A61B 5/021* (2006.01)
   *A61B 5/0245* (2006.01)
   *A61B 5/08* (2006.01)
   *A61B 5/145* (2006.01)

(52) U.S. Cl.
   CPC ........... *G06F19/3443* (2013.01); *G06F 19/36* (2013.01); *G06K 9/00536* (2013.01); *A61B 5/021* (2013.01); *A61B 5/0245* (2013.01); *A61B 5/0816* (2013.01); *A61B 5/145* (2013.01); *A61B 2560/0276* (2013.01)

USPC ............... 702/181; 702/19; 702/67; 702/189; 600/301; 600/484; 600/512; 600/544

(56) References Cited

U.S. PATENT DOCUMENTS 8,290,575 B2 * 10/2012 Tarassenko et al. .......... 600/512
   8,398,555 B2 * 3/2013 Ochs et al. .................... 600/484
   8,412,655 B2 * 4/2013 Colman et al. .................. 706/16
   8,414,488 B2 * 4/2013 Colman et al. ................ 600/301
   8,547,248 B2 * 10/2013 Zdeblick et al. ......... 340/870.28
   8,666,467 B2 * 3/2014 Lynn et al. .................... 600/323
   8,690,771 B2 * 4/2014 Wekell et al. ................. 600/301
   2004/0148140 A1 * 7/2004 Tarassenko et al. .......... 702/189

* cited by examiner

NOVELTY DETECTION WITH MISSING PARAMETERS

CROSS-REFERENCE TO RELATED APPLICATIONS

This application is a 371 U.S. National Stage of International Application No. PCT/GB2009/002408, filed Oct. 9, 2009. This application claims priority to British patent application No. 0818544.9 filed with the Intellectual Property Office on Oct. 9, 2008, which is herein incorporated by reference in its entirety.

The present invention relates to multi-parameter monitoring and in particular to improvements in methods and systems for monitoring the state of a system by repeated measurements of a plurality of different system parameters using different sensors.

The need to monitor the state of a system by monitoring, or repeatedly measuring, a variety of different parameters of the system arises in wide variety of fields: for example in the engineering field by monitoring physical systems such as complex machines, industrial plant and the like, and in the medical or veterinary field by monitoring biological systems such as humans or animals. Traditionally where multiple parameters have been monitored, an output has been provided for each parameter being monitored, but as the number of monitored parameters increases, it becomes increasingly difficult for an operator to make sense of the multiple outputs and to spot abnormal states of the system being monitored. A simple way to overcome this problem has been to establish a threshold on each of the parameters, and to output an alarm signal to the operator if the threshold is breached. But it is very difficult to set appropriate thresholds in complex systems. The inappropriate setting of thresholds can result in abnormal states not being notified to the operator, or in too many alarms being generated. Missing abnormal system states is clearly undesirable, but it is equally undesirable to avoid over-alarming as operators tend then to ignore alarms.

Proposals have been made for automatically interpreting parameter measurements in a more intelligent way. Few such proposals, however, have engendered sufficient trust on the part of operators to be useful in practice. One such "intelligent" system which is used in practice in a clinical setting is the patient condition display disclosed in WO-A-2-02/096,282 of which the current commercial version is the "Visensia" system from Oxford Biosignals Ltd. This relates to a multi-parameter monitoring system used in the clinical environment, in particular for monitoring patients in high-dependency or intensive care units. Such patients typically have several vital signs monitored, such as electrocardiogram (ECG), respiration (for instance measured by electrical impedance pneumography), oxygen saturation (for instance measured by pulse oximetry with a finger probe), blood pressure and body temperature. Of course other vital signs may be measured, and it is also possible to derive from the primary measurements secondary parameters such as heart rate, heart rate variability, respiration rate and so on.

Typically these parameters are collected at different rates, for instance the ECG (giving heart rate) at 250 Hz, the pulse oximeter signal at 81.3 Hz, the respiration at 64 Hz, the temperature at 1 Hz, and blood pressure once every 30 to 60 minutes.

In the techniques disclosed in WO-A-2-02/096,282 the parameter measurements are collected into contemporaneous sets of values (each value being one measurement of one of the parameters) and each set is regarded as defining a data point x in a multi-dimensional measurement space. Thus if, say, five parameters are being measured, the multi-dimensional measurement space is 5-dimensional, such that the data point is defined by the five values of the parameters $x(x_1, x_2, x_3, x_4, x_5)$. As it is impossible to display clearly a 5-dimensional space, WO-A2-02/096/282 proposes on the one hand displaying data points in a reduced-dimensionality visualization space, and on the other hand the calculation of a one-dimensional "novelty index" which is based on the Euclidian distance between a given data point and a set of prototype points representing normality for the patient or patient group. Thus a data point which is based on parameter measurements which are quite abnormal would be a greater distance from normality in the 5-dimensional measurement space. Normality is defined by examining a training set of thousands of data points and then finding a greatly reduced number of cluster centres. These cluster centres are then regarded as the prototype points. Each new incoming data point representing the current state of the patient is then compared with the prototype points to find the distance from them (i.e. Euclidian distance in the 5-dimensional measurement space) and this is used to derive a novelty index. A threshold is placed on the novelty index and if the threshold is exceeded, an alarm can be generated to call the attention of clinical staff to the patient. In the particular example in WO-A2-02/096,282 the novelty index is based on the Parzen Windows probability density function:

$$p(x) = \frac{1}{N(2\pi)^{d/2}\sigma^d} \sum_{i=1}^{N} \exp\left\{-\frac{1}{2\sigma^2}\sum_{j=1}^{d}(x_j - x_{ij})^2\right\} \quad (1)$$

where:
  $x_j$ for j from 1 to d are the measured parameters of a data point x, e.g. d=5 for the parameters heart rate, respiration, oxygen saturation, blood pressure and temperature;
  $x_{ij}$ are the corresponding parameter values of the N prototype points $x_N$
  and $\sigma$ is a global width assigned to all of the prototype points and its value is established using a variety of methods; for example, by making it equal to the average of the distance to the ten nearest neighbours.

The novelty index (commercially the Visensia Index) is defined as:

Novelty Index=$-\log p(x)+c$

Where c is a constant offset to ensure that a normal input has a score of zero. In the Visensia Index c=6.0.

The use of the novelty index and generation of alarms based on a novelty index threshold has been very successful in practice.

However a problem exists in the event that a signal from one of the sensors is lost or missing. For example, it is not unusual for sensors to be disturbed to or to fall off a patient (for example ECG electrodes or pulse oximetry finger probes) and occasionally sensors malfunction or measurements are missed for some reason. To be robust the system needs to cope with such an eventuality.

An approach in this type of multi-parameter measurement system has been to replace a missing parameter by its mean value. This allows the system to continue processing the inputs despite loss of one or more parameter measurements. Although this makes the system robust, it can result in misinterpretations which are potentially dangerous. This is because replacing a missing parameter by its mean value amounts to assuming that the parameter is normal. If the overall state of the system being monitored is being interpreted on the basis of a combination of different parameters, forcing one of those parameters to be normal clearly tends to influence the overall interpretation towards normality. Thus an abnormal state might be missed because of the assumption that the missing parameter is normal.

One aspect of the present invention therefore aims to provide an improved way of coping with lost sensor outputs. This is achieved by ensuring that a reduced dimensionality evaluation of the system state (such as the novelty index) is generated on a consistent scale regardless of variations in dimensionality of the input. The invention also allows the detection of sensor malfunction by determining whether a change in the reduced-dimensionality evaluation of the system state is being caused by a change on a single sensor.

The novelty index mentioned above and disclosed in WO-A2-02/096,282 has proved to be a useful measure but because it is calculated in the multi-dimensional measurement space, its actual value depends on the number of dimensions of that space. It would be useful to be able to calculate the novelty index on a consistent basis for increased dimensionality data sets (as well as for data sets with decreased dimensionality through signal loss as above). Another aspect of the invention therefore provides a way of calculating a reduced-dimensionality evaluation of system state, such as the novelty index, on a consistent scale for increased as well as decreased dimensionality input data sets.

Loss of One or More Parameters in Real Time Monitoring

A first aspect of the invention provides method of determining and displaying an index of novelty representing the state of a system based on measurements of a plurality of different parameters of the system, the plurality of parameters defining respective dimensions of a multi-dimensional measurement space, the method comprising the steps of:

receiving sets of values each value in a set being a measurement of a different one of said plurality of parameters, each set defining a data point in said multi-dimensional measurement space;

calculating the index of novelty for each data point by comparing the position in said multi-dimensional measurement space of each data point to a set of prototype data points comprising measurements of said parameters representative of the system being in a normal state, wherein in the event of receipt of a deficient data point missing one or more of said parameter values of said set, the method further comprises the steps of:

calculating a marginal index of novelty of the deficient data point by comparing the position of the deficient data point to the set of prototype data points in a reduced dimensionality space omitting the dimensions corresponding to the missing parameter values, using a predefined relationship, calculated for said reduced dimensionality space, between the marginal index of novelty and the marginal probability of different states of the system to find a marginal probability value representing the probability of the system being at least as close to said normal state as the state represented by the deficient data point, using a further predefined relationship, calculated for said multi-dimensional measurement space, between the index of novelty and the probability of different states of the system to find the index of novelty in said multi-dimensional measurement space corresponding to a probability equal to said marginal probability value; and displaying the index of novelty so found as the index of novelty for the deficient data point.

Thus the invention utilises a probability value to allow the consistent calculation of novelty index regardless of variations of dimensionality of the incoming data point.

Preferably, in calculating the index, or marginal index, of novelty for each data point its position is compared to the set of prototype data points using a probability density function based on the Euclidian distance between that data point and each of the prototype data points. The probability density function may be the Parzen Windows function defined by Equation (1) above. The prototype points may be cluster centres in a training set of multiple samples of data points, and the same cluster centres may be used in calculating the marginal index of novelty in the reduced dimensionality space regardless of which parameter values are missing. However as an alternative new cluster centres may be calculated in each reduced dimensionality space.

The predefined relationships linking probability and novelty index both in said reduced dimensionality space and in said multi-dimensional measurement space may be based on a training set of multiple samples of data points. The relationships may be based on taking as thresholds values of the index, or marginal index, of novelty progressively ranging from a minimum to a maximum value, finding for each of said thresholds the fraction of data points in the training set which have an index, or respectively marginal index, of novelty below the threshold, and taking that fraction as the probability value, or respectively marginal probability value, for that index, or respectively marginal index, of novelty. The same single training set of data points may be used for each different reduced dimensionality space, each time omitting a different parameter or combination of parameters from the sets of values forming each data point of the training set The invention also provides apparatus for determining and displaying an index of novelty representing the state of a system based on measurements of a plurality of different parameters of the system, the apparatus comprising an input for receiving said measurements of a plurality of different parameters, a processor adapted to execute the method steps above, and a display for displaying the index of novelty.

Find Novelty Index for New Data Set with More Parameters

Another aspect of the invention provides a method of determining and displaying an index of novelty representing the state of a system based on measurement of a plurality of different parameters of the system, the method comprising the steps of:

receiving a data set comprising a plurality of sets of values each value being a measurement of a different one of said plurality of parameters, each set of values defining a data point in measurement space of dimension D, where D is a positive integer greater than one;

calculating a provisional index of novelty for each data point by comparing the position in said measurement space of dimension D of each data point to a set of prototype data points comprising measurements of said parameters representative of the system being in a normal state;

calculating a relationship, in said measurement space of dimension D, between the provisional index of novelty and the probability of different states of the system to find a probability value representing the probability of the system being at least as close to said normal state as the state represented by a data point having that provisional index of novelty, using said calculated relationship to find for each data point of the data set the probability value corresponding to its provisional index of novelty;

using a further predefined relationship between the probability of different states of the system and an index of novelty defined in a space of dimension L, where L is a positive integer less than D, and based on comparing the distance between a data point and said prototype data points, to find for each data point of the data set the index of novelty corresponding in the space of dimension L to said probability value; and displaying the index of novelty so found as the index of novelty for that data point.

Preferably in calculating the index, or provisional index, of novelty for each data point its position is compared to the set of prototype data points using a probability density function, such as the Parzen Windows function, based on the Euclidian distance between that data point and each of the prototype data points.

The predefined relationships linking probability and novelty index both in the increased D-dimensional space and in the lower L-dimensional space may be based on a training set of multiple samples of data points. The relationships may be based on taking as thresholds values of the novelty index progressively ranging from a minimum to a maximum value, finding for each of said thresholds the fraction of data points in the training set which have a novelty index below the threshold, and taking that fraction as the probability value for that novelty index.

This aspect of the invention also provides apparatus for determining and displaying a consistent index of novelty representing the state of a system based on an increased dimensionality data set using the method above, and a display for displaying the index of novelty.

Detection of Sensor Fault

A third aspect of the invention provides a method of detecting sensor malfunction amongst a plurality of different sensors each measuring a parameter of the system, the plurality of parameters defining respective dimensions of a D-dimensional measurement space, where D is equal to the number of sensors, the method comprising the steps of:

receiving sets of values, each value in a set being a measurement from a different one of said sensors, each set defining a data point in said D-dimensional measurement space;

calculating an index of novelty for each data point by comparing its position in said D-dimensional measurement space to a set of prototype data points comprising measurements of said parameters representative of the system being in a normal state;

using a predefined relationship, calculated for said D-dimensional measurement space, between the index of novelty and the probability of different states of the system to find a probability value representing the probability of the system being at least as close to said normal state as the state represented by the data point;

calculating for each data point at least one marginal novelty index by ignoring one parameter value from said set of values and comparing the position of the data point in a D-1 dimensional space to the set of prototype data points also in the D-1 dimensional space, the D-1 dimensional space omitting the dimension corresponding to the ignored parameter;

using a further predefined relationship, calculated for said D-1 dimensional space, between the marginal index of novelty and the marginal probability of different states of the system to find a marginal probability value representing the probability of the system being at least as close to said normal state as the state represented by the marginal novelty index;

comparing said probability value and said marginal probability value; and in the event of the probability value and marginal probability value differing by more than a predefined threshold, outputting an alert for malfunction of the sensor whose parameter value was ignored.

Preferably the method further comprises repeating the steps of calculating a marginal novelty index and finding a marginal probability value for each data point, each time ignoring a different parameter value, and comparing each resulting marginal probability value to the probability value, to check for malfunction of each of said sensors.

Preferably the alert is output if only one of the marginal probability values differs by more than a predefined threshold from said probability value.

The novelty index may be calculated as using a probability density function based on the Euclidian distance, such as the Parzen Windows function, between that data point and each of the prototype data points. The prototype points may be cluster centres in a training set of multiple samples of data points, and as before the same cluster centres may be used in calculating the marginal index of novelty in the D-1 dimensionality space regardless of which parameter value is missing, though alternatively new cluster centres may be calculated for each D-1 dimensional space.

Again as before the predefined relationships in said D-1 dimensionality space and in said D-dimensional measurement space may be based on a training set of multiple samples of data points. They may be based on the same approach of thresholding novelty index values to find the probability value for that index of novelty.

This aspect of the invention also provides apparatus for detecting sensor malfunction amongst a plurality of different sensors each measuring a parameter of the system, the apparatus comprising an input for receiving inputs from said sensors, a processor adapted to execute the method above, and a device for outputting said alert.

The various aspects of the invention are applicable to a variety of systems undergoing multi-parameter monitoring, including particularly biological systems such as humans or animals, and where the parameters are medical measurements. Thus the invention may be applied to medical monitoring devices. As an example, the parameters measured may be the five vital signs mentioned above, namely heart rate (from ECG), blood pressure, temperature, Oxygen saturation (SaO2), breathing rate, and others such as Glasgow Coma Scale (GCS) score.

The data processing steps in the methods of the invention may be embodied in software. Thus the invention extends to computer programs comprising program code means to execute the methods of the invention on a data processor, and to storage means such as data carriers carrying such computer programs.

The invention will be further described by way of example with reference to the accompanying drawings, in which.

Figure 6:
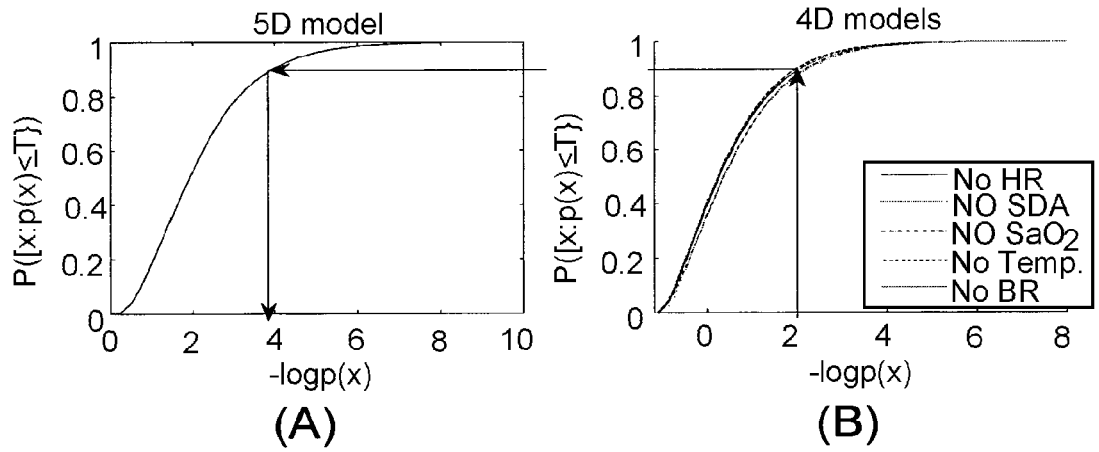
Figure 7:
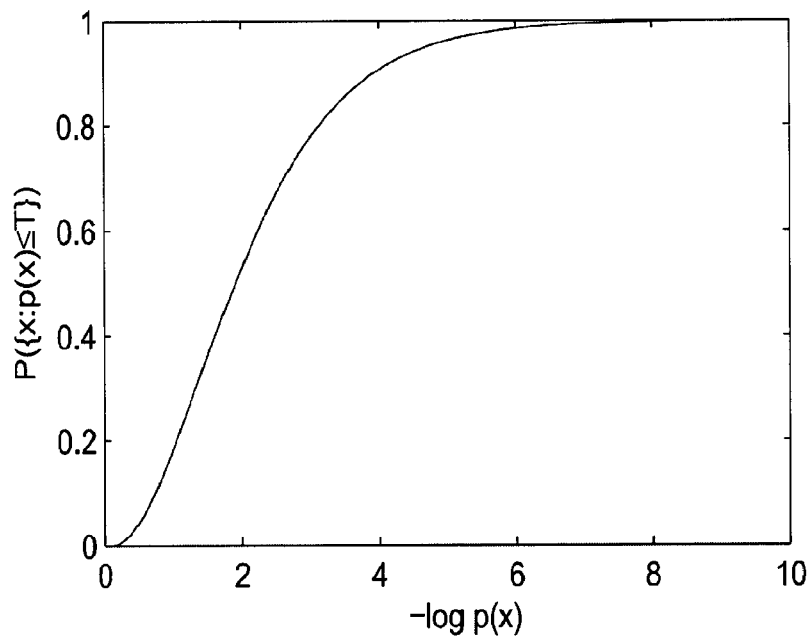
Figure 8:
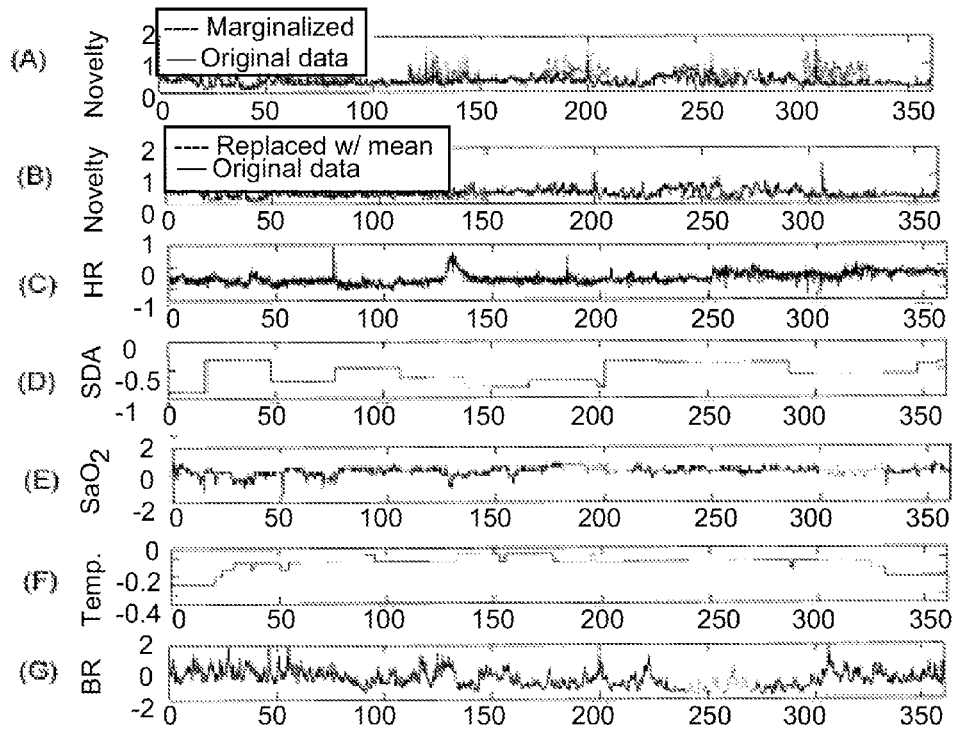
Figure 9:
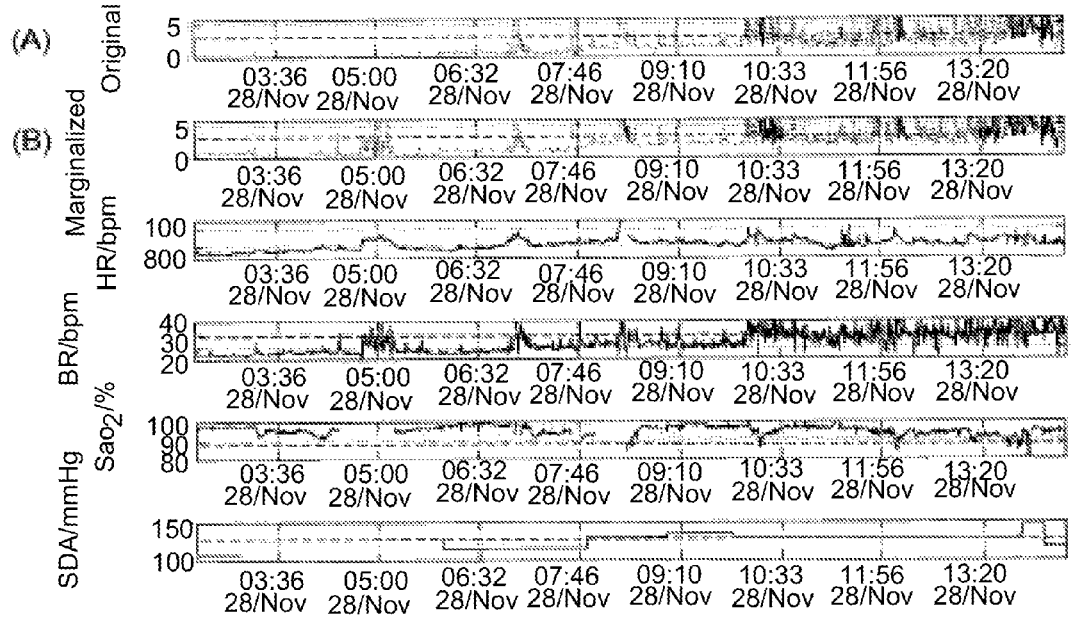

FIGS. 6(A) and (B) illustrate curves relating to novelty index and probability and marginal novelty index and marginal probability in different dimensionality data sets;

FIG. 7 illustrates the calculated relationship between novelty index and probability for a sample five dimensional set;

FIG. 8 (A) to (G) illustrates the operation of an embodiment of the invention on a 12 hour multi-parameter recording of vital signs data from a patient, with artificially generated periods of data loss; and FIG. 9 illustrates the effect of re-calculating the novelty index on the generation of alerts in a sample twelve hour multi-parameter recording of vital signs data for a particular patient.

Figure 1:
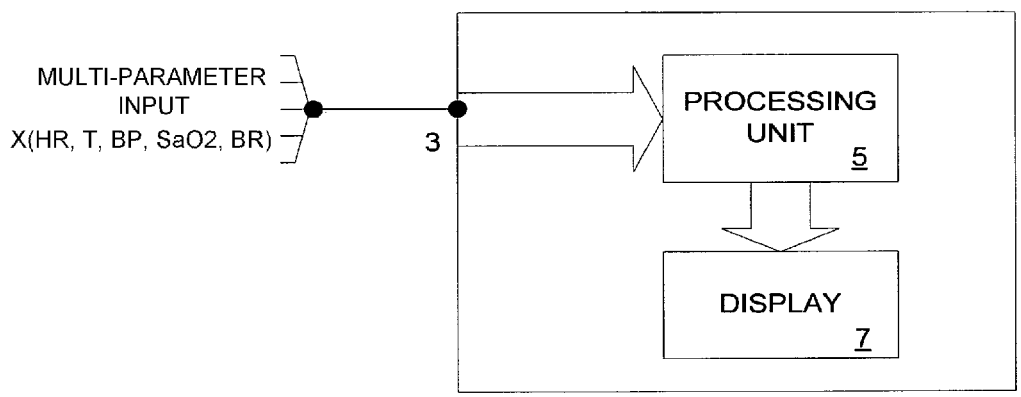
FIG. 1 illustrates schematically an apparatus in accordance with an embodiment of the invention.

FIG. 1 schematically illustrates an apparatus in accordance with an embodiment of the invention. The apparatus is provided with an input 3 for receiving signals from multiple sensors each measuring a parameter of the system being monitored. For example, in the case of a clinical monitor, the inputs could be the heart rate, blood pressure, oxygen saturation, body temperature and breathing rate. These are measured on a continual basis, but at different collection rates, as mentioned above. The measured values are input to a processor 5 which processes the parameter measurements as will be explained in detail below and on the basis of these measurements outputs on the display 7 an indication of the state of the patient.

For convenience the parameter measurements are grouped into sets of contemporaneous values, one for each parameter, so that each set consists of, for example, a heart rate measurement, a temperature measurement, a blood pressure measurement, an oxygen saturation measurement and a breathing rate measurement. It will be appreciated that for parameters which are only collected for a relatively low rate the same measurement may appear in several successive sets of values. Each set of values can be regarded as defining a data point in a multi-dimensional measurement space. In the above example there are five parameter values in each set so the measurement space is 5-dimensional.

This embodiment of the invention is designed to cope with loss of one or more of the parameter measurements for example because of sensor malfunction, and to provide a novelty index measurement which has a consistent meaning regardless of the number of different parameters available at any given time.

Figure 3:
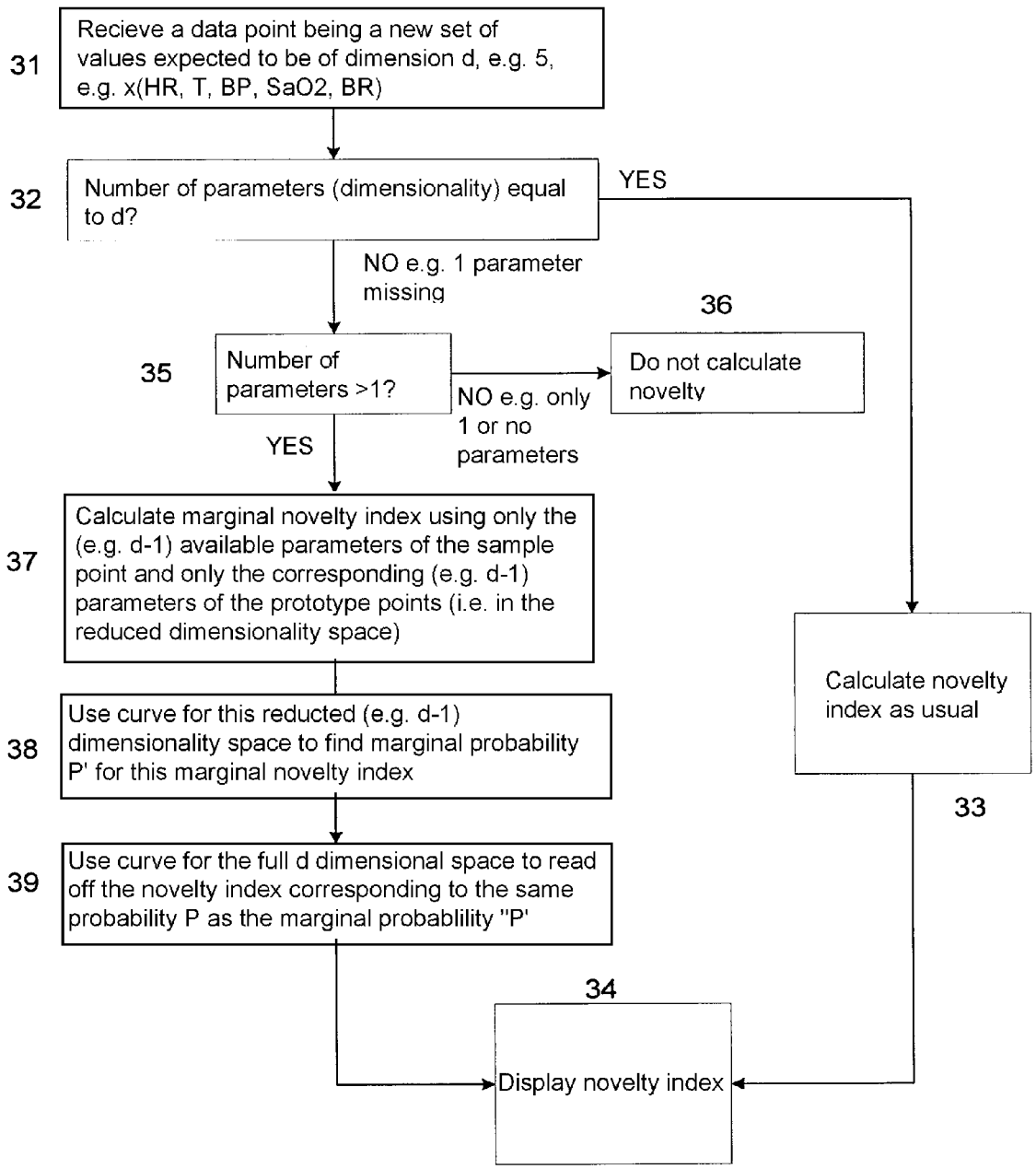
FIG. 3 is a flow diagram explaining the operation of an embodiment of the invention in the case of reception of a data point with one or more lost parameter values.

Referring, therefore, to FIG. 3 which illustrates the overall functioning of the apparatus, after reception of a new set of values at step 31, the set is checked at step 32 to determine whether any parameters are missing. For example, if the system is monitoring the five vital signs mentioned above there should be five parameters corresponding to a dimensionality d in the measurement space of 5. If the number of parameters is 5 as expected then processing passes to step 33 in which the novelty index is calculated as explained above by evaluating the quantity:

$$\text{Novelty Index} = -\log p(x) + c \quad (2)$$

where:

$$p(x) = \frac{1}{N(2\pi)^{d/2}\sigma^2} \sum_{i=1}^{N} \exp\left\{-\frac{1}{2\sigma^2} \sum_{j=1}^{d} (x_j - x_{ij})^2\right\} \quad (1)$$

This novelty index is then displayed on display 7 at step 34 and is optionally compared to a threshold for generation of an alert if the threshold is exceeded. In the example below and in the present commercial implementation of the device of WO-A2-02/096,282 a novelty threshold of 3.2 used. Thus data points whose novelty index exceeds 3.2 cause an alert to be generated.

Inspection of Equation (I) above reveals that the novelty index is based on the distance in the multi-dimensional measurement space between the data point x and the multiple prototype points $x_N$ i.e. $|x-x_N|$. In the event of one or more parameters being missing, it is undesirable, as explained above, to replace those parameters with their mean values in order to allow the calculation of novelty index to be made. In this embodiment of the invention a better approach is adopted which is analogous to the process of marginalization in probability theory. Marginalization refers to the calculation of the probability of one event regardless of some other event happening. This "marginal probability" is found by summing the joint probability over the unrequired event. The inventors have found that under the assumption that all of the variables are Gaussian and unrelated, marginalization of one parameter is equivalent to ignoring it.

In the application of this idea to the calculation of the novelty index, therefore, it is possible to calculate a new marginal novelty index in a reduced dimensionality space simply omitting the dimension corresponding to the missing parameter.

It should be noted that if so many parameters are missing that only one or none are left, novelty is not calculated, this being checked and provided for in steps 35 and 36 of the process as shown in FIG. 3.

Assuming, for example, that one parameter is missing, then in step 37 of FIG. 3 a marginal novelty index is calculated using only the (d-1) parameters of the newly received data point and only the same corresponding (d-1) parameters of the multiple prototype points. For example if the oxygen saturation value is missing from a newly received data point, then the distance calculation in Equation (1) is conducted in only a 4-dimensional measurement space using only the 4 parameters of heart rate, temperature, blood pressure and breathing rate for both the newly received data point and the N prototype data points.

Although this calculation produces a numerical value for the marginal novelty index, it should be appreciated that this numerical value will not necessarily be equal to the value of the novelty index that would have been generated had all 5 dimensions been present.

In order to achieve a consistent scale for novelty index across different dimensionalities, therefore, the invention provides a way of converting the marginal novelty index calculated in step 37 onto a normal novelty index scale which is consistent with the novelty index calculated for the full 5 dimensions. In particular this is achieved by converting the novelty indexes into a probability value based on all the states in the training set. The probability of the system being in a particular state does not vary with the number of dimensions used to describe that state and thus it provides a convenient consistent way of converting between different dimensionality spaces. Thus having found a probability value corresponding to a marginal novelty index in (d-1) dimensions, we look for a novelty index in d dimensions which give the same probability value.

In the present embodiment curves as shown in FIGS. 6A and B relating the novelty index to the probability are prepared for each of the different dimensionality spaces (as will be explained in more detail below) and thus in step 38 the curve appropriate for the (d-1) dimensionality data set of FIG. 6B is used to read off the marginal probability value corresponding to the marginal novelty index obtained in step 37.

Then in step 39 the similar curve for the d-dimensional data (e.g. 5D) set as shown in FIG. 6A is used to find that novelty index (e.g. in 5 dimensions) which has the same probability as the marginal probability found in step 38. The novelty index found in step 39 is then displayed in step 34 as the novelty index for that data point.

FIG. 6B illustrates the five curves relating marginal probability and marginal novelty index for each of five 4-D spaces calculated from a training set of data by, in turn, omitting the heart rate, blood pressure, oxygen saturation, temperature and breathing rate. The five curves are similar, though slightly different as shown. FIG. 6A illustrates the corresponding curve for the 5 dimensional data set in which all five parameter values are present. As illustrated in FIGS. 6A and B, if a data point in the 4-dimensional data set omitting the heart rate parameter gives a novelty index of two, this corresponds to a marginal probability of 0.891 (this being read-off as the marginal probability value P' in step 36). In FIG. 6A the probability value of 0.891 corresponds to a novelty value of 3.8 (this being read-off as the novelty index in step 37). Thus 3.8 is the appropriate novelty index for display for such a data point lacking the heart rate parameter.

Figure 2:
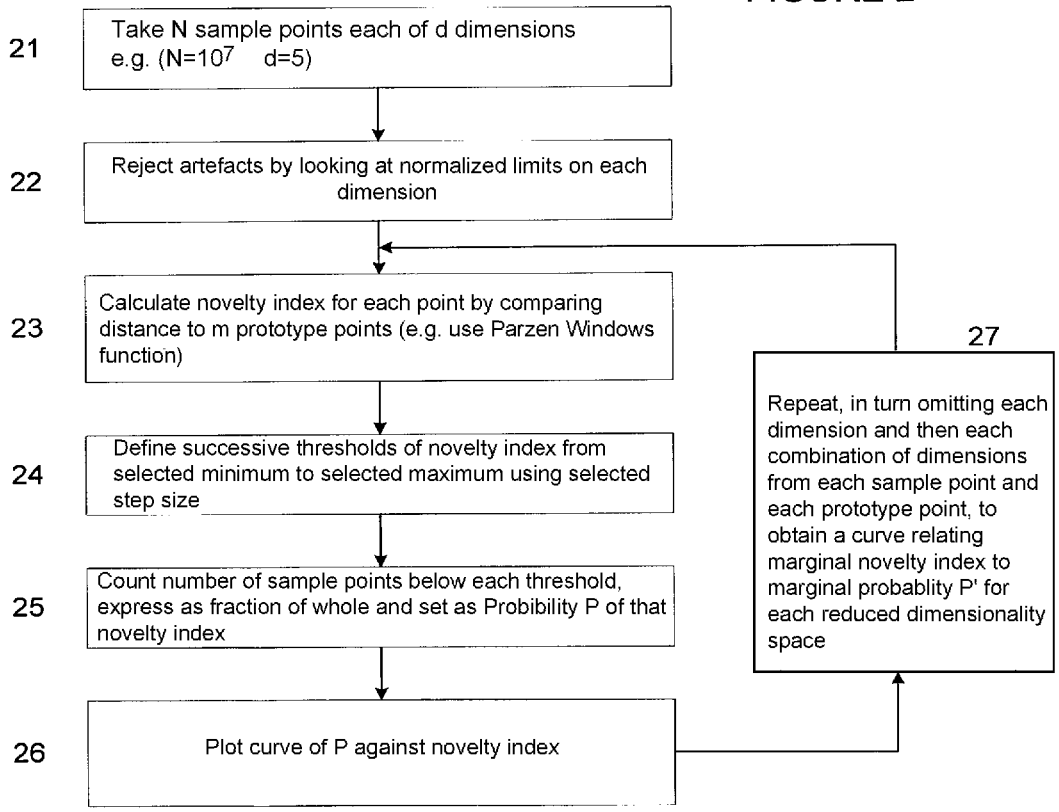
FIG. 2 is a flow diagram explaining the calculation of a relationship between probability and novelty index in an embodiment of the invention.

FIG. 2 illustrates how curves such as those shown in FIGS. 6A and B are calculated for use in steps 36 and 37 of the method. In order to convert the novelty index values to probability values it is necessary to have a training set of sample data points. This embodiment of the invention uses a training set of 10 million data points generated by sampling the distribution estimated, using Parzen windows, from the training data. Thus in step 21 of FIG. 2 the N (=10 million) sample points, each of d (e.g. 5) dimensions is taken and in step 22 an artefact rejection process is applied using upper and lower bounds for each parameter based on physiological knowledge. For example the upper bound on heart rate is 300 beats/min and the lower bound is 30 beats/min. Samples outside the upper and lower bounds are rejected as they are physiologically implausible.

Then the novelty index is calculated for each sample point remaining after artefact rejection. This involves evaluating Equations (1) and (2).

As mentioned above the inventors have found that a way of relating novelty indexes (which are based on probability density) generated in spaces of different dimensionality is to use a probability value (which by definition lies between 0 and 1) and which represents the probabilities of different system states compared to all of the system states in the training set. Thus although the novelty index value may vary with dimensionality for the same system state, probability provides a consistent scale regardless of the dimensionality. The probability depends on the information available. If only heart rate and breathing rate data are available and they are abnormal, the probability will be lower than if the same heart rate and breathing rate data were available as well as a completely normal blood pressure. The increased information about the system state changes the probability.

To find such a probability value, therefore, in step 24 a series of successive "thresholds" of novelty index are defined from a minimum expected novelty index to a maximum expected novelty index, and for each threshold the number of sample points which have a lower novelty index than that threshold is counted. This number, expressed as a fraction of the total number of samples, gives the probability that the system is in a state which is equal to or closer than normality than the state implied by that novelty index threshold. The maximum and minimum expected novelty indexes can be freely chosen by inspection of the training set and in the current example a minimum novelty index of 1.83 and a maximum of 40.04 were chosen. Successive novelty index values separated by step size of 0.01 were then generated and the number of samples with the novelty index less than each successive threshold were counted.

FIG. 7 shows the resulting values of probability for each successive novelty index threshold as plotted in step 25 for values of $-\log p(x)+6.0$ between 0 and 10 (corresponding to novelty index values calculated by Equation (2). FIG. 7 is the plot for the full five-dimensional data set. In step 26 the process is repeated for each four-dimensional data set obtained by ignoring a different one of the five parameters. The process is again repeated for each three-dimensional data set obtained by ignoring a different two of the five parameters, and then again for each two dimensional data set obtained by ignoring a different three of the five parameters. Thus in all 26 different curves are obtained for each possible different dimensionality of the data set.

It should be noted that although the prototype points representing normality could be recalculated for each different dimensionality data set (by recalculating the prototype points in the appropriate dimensionality), for simplicity in this embodiment the same prototype points were used for each dimensionality, simply ignoring the relevant parameter or parameters being omitted.

FIG. 6A illustrates the curve for the five dimensional model alongside in FIG. 6B the five different curves for the five different 4D models.

FIG. 8 illustrates the results of applying the method of FIG. 3 to a six-hour recording of all five vital signs for a patient in which in certain periods one, two or three of the parameters is (artificially) removed and the novelty index is valuated by the method of FIG. 3, and for comparison by replacing the lost parameter by its mean value. This therefore replicates the effect of sensor malfunction or loss.

FIG. 8(A) the novelty index calculated using marginalization of any missing parameters (dotted) is shown compared with the output generated using the original 5D model using all the original data (solid). As a further comparison, FIG. 8(B) shows handling missing parameters by replacing the missing parameters with their mean in the training data and calculating the novelty index using the original 5D model. This is shown in dotted line, and again the novelty calculated using all of the data is shown in solid line.

FIGS. 8(C) to (G) show each of the vital signs used to calculate the novelty index. The plotted values are dotted when the vital sign is removed from the calculation used to generate the dotted data in the top two plots (FIGS. (A) and (B)). For the comparison six one-hour segments along the time axis were defined. The first segment corresponds to all the vital signs being available for the entire hour. The second to sixth segments each correspond to an initial thirty minute period with a different combination of missing vital signs and second thirty minute period with all the vital signs available.

The period from 0 to 60 minutes in FIG. 8 corresponds to all the vital signs being available and as a consequence all four novelty index traces (solid and dotted in both FIGS. 8(A) and (B), are identical. Between 60 and 90 minutes temperature is removed from the calculation, and the temperature trace is therefore dotted. The recorded temperature value is very close to the mean in the training dataset (36.05° C.). As a result of this, it is difficult to differentiate the novelty index calculated by replacing the missing parameter with its mean in the training data (dotted in FIG. 8(B)) from the novelty index calculated using all of the original data (solid). In FIG. 8(A), the novelty index corresponding to the marginalized model (dotted) is higher than that calculated using all the data (solid). There is no longer the knowledge that temperature has a normal value, therefore in the absence of this information the pattern (system state) comprising the other four vital signs appears more unusual and the novelty index is correspondingly higher than that calculated higher than that calculated using all the data (solid).

In the period from 90 to 120 minutes all five vital signs are once more available and all four novelty index plots are identical. Between 120 and 150 minutes both blood pressure (SDA) and temperature are artificially removed. Temperature is again close to its mean in the training data and SDA is 0.86 standard deviations above the mean value in the training dataset (94.7 mmHg). As both values are fairly normal, in FIG. 8(B), the novelty index calculated by replacing the missing parameters with the mean in the training data (dotted) is close to the novelty index calculated using all the data (solid); although as the assumption that both parameters are equal to the mean is not correct, the novelty index calculated using the actual values is a littler higher. In FIG. 8(A) the novelty index calculated using the marginalized model of FIG. 3 (dotted) is significantly higher than novelty calculated using all the data (solid). The abnormality of the heart rate, breathing rate and blood oxygen saturation without the context of a normal temperature and SDA causes the novelty index to be higher than when the values of the other parameters are also used.

During the period from 150 to 180 minutes all five vital signs are once more available and all four novelty index plots are identical. Between 180 and 210 minutes both blood oxygen saturation and temperature are artificially removed. The temperature is lower during this period, ranging from 0.35 and 0.66 standard deviations below the mean. The blood oxygen saturation is 100% and therefore 1.4 standard deviations above the mean in the training data. As both missing parameters are some distance from the mean, the novelty index calculated assuming they are equal to the mean in the training data (dotted in FIG. 8(B)) is considerably lower than the novelty index (solid) calculated using the true values. In FIG. 8(A) the novelty index calculated using the marginalized model is close to that calculated using all the vital signs values. Marginalization has made no assumption about the missing parameters and in the absence of information about them, the novelty index calculated from the remaining three parameters is high.

From 210 to 240 minutes all five vital signs are once more available and all four novelty plots are identical. During the period between 240 and 270 minutes blood pressure (SDA), temperature and breathing rate are all artificially removed, i.e. only heart rate and blood oxygen saturation are used to calculate the novelty index shown dotted in FIGS. 8(A) and (B). During this period SDA is 1.1 standard deviations above the mean, temperature is 0.3 standard deviations below the mean, and breathing rate is between 1.6 standard deviations below the mean and 0.9 standard deviations above the mean. As two of the three missing parameters are approximately one standard deviation from the mean, when they are replaced with the mean value of the training data to produce the novelty index in FIG. 8(B), the novelty index is lower than that calculated using the true values (solid). In this period heart rate is between 0.4 standard deviations below the mean and 0.93 standard deviations above the mean, and blood oxygen saturation remains 1.4 standard deviations above the mean. The novelty index plotted dotted FIG. 8(A) is considerably higher than that calculated using data for all five parameters. The reason for this is that without the context of the SDA, temperature and breathing rate measurements, the unusual pairs of blood oxygen saturation and heart rate values have low probability.

In the period from 300 to 330 minutes all five vital signs are once more available and all four novelty index plots are identical. Between 330 and 360 minutes SDA, blood oxygen saturation, and temperature are all artificially removed, i.e. only heart rate and breathing rate are used to calculate the novelty index in the two dotted plots. SDA and blood oxygen saturation are 1.1 and 1.4 standard deviations above the mean, respectively; and temperature is 0.2 standard deviations below the mean. As a result of two of the missing parameters being more than one standard deviation from the mean, the novelty index calculated by replacing the missing parameters with the mean in the training data (dotted in FIG. 8(B)) is considerably lower than the novelty index calculated using all the vital signs data (solid). In FIG. 8(A), novelty calculated using the marginalized model (dotted) is closer to that calculated using all of the available data.

During the period from 300 to 330 minutes the heart rate varies between 0.33 standard deviations below the mean and 0.4 standard deviations above the mean, and the breathing rate varies between 1.2 standard deviations below the mean and 1.1 standard deviations above the mean. In FIG. 8(A) novelty calculated using these values in the marginalized model (dotted) is on average close to that calculated using all of the vital sign data. It should be noted that the novelty index calculated using the marginalized model is more sensitive to the perturbations in breathing rate and heart rate, above and below the mean in the training data, than the novelty index calculated using all five parameters. This is because without conditioning the probability of the heart rate and the breathing rate on the other three parameters, the small deviations in the value of the heart rate breathing rate have a more significant effect on the probability of the vital signs pattern (system state). The final 30 minutes of the figure (330 to 360 minutes) correspond to all the models using all the vital signs data and once again the four novelty index traces are identical.

As mentioned in the introduction, one application of the calculation of novelty index is its use in generating alerts when a patient's condition departs from normality by more than a threshold amount. FIG. 9 illustrates the effect of re-calculating the novelty index as explained above on the generation of alerts in a sample twelve hour recording for a particular patient.

FIG. 9 shows the novelty and vital signs for such a 12 hour period. FIG. 9(A) shows the novelty index and alerts generated using the original model in which mean values are used to replace missing parameters. FIG. 9(B) shows the novelty index calculated using the method of the invention. During the periods when the heart rate, breathing rate, blood oxygen saturation and SDA are all available the two novelty index plots are similar e.g. between 02:30 and 03:00. The novelty indexes are not identical as the novelty index calculated using the invention tends to be a little higher. This is because the invention does not make the assumption that the temperature data, absent from the entire recording, is equal to its mean in the training data (and therefore normal).

When two parameters are missing e.g. between 03:00 and 04:30, both novelty indexes are close, although the novelty index is again higher as it is not assumed that both missing parameters (temperature and SDA) are normal. When three parameters are missing e.g. between 04:30 and 05:15 the novelty index is only calculated using the method of the invention (FIG. 9(B)) and the abnormal high breathing rate contributes to a high value of novelty index that crosses the alert threshold of 3.2 for a short period. During this period, the method of the invention enables the calculation of novelty index during a period of unusual vital signs when only heart rate and breathing rate information is available. As can be seen from FIG. 9(A), the replacement by mean method does not return a novelty index at all during such periods.

An extra alert can be seen in FIG. 9(B) at 08:30. Although novelty index calculated using both models crosses the threshold, an alert is not generated by the original model for two reasons. Firstly, there are times when no novelty index is calculated by the original model because both heart rate and blood oxygen saturation are missing. Secondly when only heart rate is missing (blood oxygen saturation being once more available) the novelty index in FIG. 9(B) is higher, as the vital sign pattern is less probable when it is not assumed that both temperature and heart rate are equal to their means in the training data (normal values).

There is an alert at 10:10 in both models; however, it lasts longer in FIG. 9(B) because the novelty index is higher. As all parameters are available, except for temperature, the higher novelty index is solely a consequence of no longer assuming that the missing temperature is normal. The alert at 12:10 is almost identical for both models. At 13:20 there is an additional alert in FIG. 9(B) only. Again all parameters are available, except for temperature, thus the higher novelty index that triggers the alert is solely a consequence of the omission of temperature. The final alert at 13:40 last fractionally longer in FIG. 9(B) for the same reason.

Handling Data Sets of Increased Dimensionality

Figure 4:
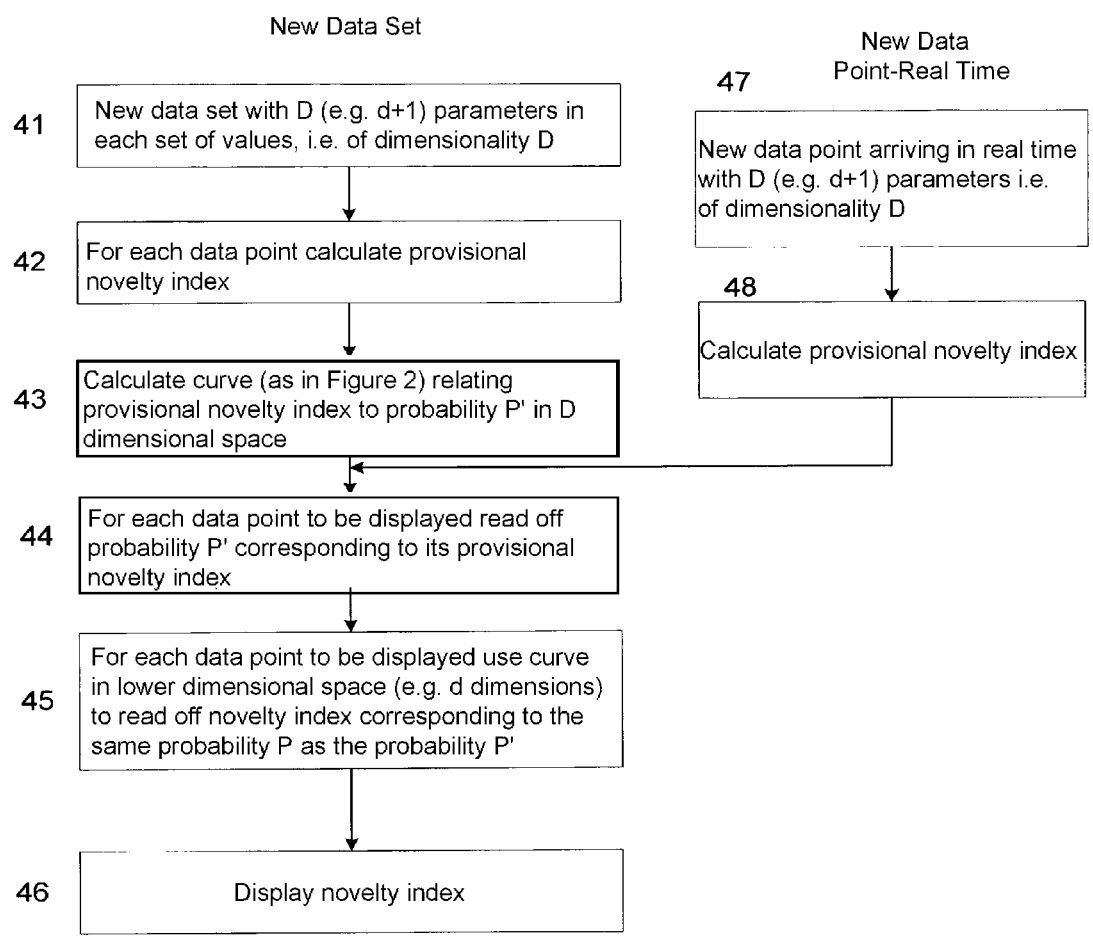
FIG. 4 is a flow diagram explaining the calculation of novelty index on a consistent scale for data sets with increased dimensionality.

The idea of using probability to allow conversion of novelty indexes between data sets of different dimensionality can be extended to handle data sets having a higher dimensionality, not only a lower dimensionality is indicated above. Such a circumstance may arise, for example, where a new data set is provided which includes measurements of another parameter, not previously measured. Again it would be useful to be able to calculate a novelty index for the new data set and for this novelty index to be on a consistent scale with novelty indexes of data sets not including that extra parameter. The inventive concept above allows this to be done. FIG. 4 illustrates in broad terms the process. For ease of understanding it will be explained with reference to the calculation of novelty index for a data set consisting of measurements of the five vital signs above on a patient, together with one additional parameter such as the Glasgow Coma Score (GCS) which is an indication of a patient's consciousness. The method is applicable, though, to the addition of two or more new parameters.

In step 41 the new data set is taken in which each data point consists of contemporaneous measurements of the five vital signs mentioned above and of the Glasgow Coma Score. Thus the data set has a dimensionality of six. More generally, in FIG. 4, this is indicated as a dimensionality D=d+1. The aim will be to calculate a novelty index which is consistent with novelty indexes calculated on data sets consisting only of five original vital signs (of dimensionality d=5). Therefore in step 42 for each data point a "provisional" novelty index is calculated in the 6-dimensional measurement space by using Equations (1) and (2). This involves comparing the distance of each data point to the multiple prototype data points representing normality. These prototype data points are calculated from a new training dataset with D=d+1 dimensions. As an alternative the probability density from the original d dimensional data set is multiplied by the one dimensional probability of the new parameter (assuming independence).

Then in step 43 the relationship between the probability of various system states and the provisional novelty is calculated to plot a curve equivalent to that shown in FIG. 7 (for D dimensions). Thus maximum and minimum values of provisional novelty index are selected and then a succession of provisional novelty index thresholds starting from the minimum and increasing by a selected step size to the maximum are taken in turn, and for each the fraction of data points with provisional novelty index less than the threshold is taken as the probability value corresponding to that provision novelty index.

Then in step 44, for each data point (or at least each data point to be displayed) the probability value corresponding to its provisional novelty index is read from the curve calculated in step 43. This probability value is used in step 45 together with the relationship calculated for the lower dimensionality measurement space (e.g. the 5-dimensional normal measurements whose relationship is illustrated in FIG. 7) to find the novelty index for 5-dimensions with the same probability value. The novelty index so found is regarded as the appropriate novelty index for that data point and is displayed in step 46. (Note that the relationship for the lower d-dimensional measurement space can be calculated from the higher, D=d+1 dimensional, data set by ignoring one parameter, or by using a d-dimensional data set.)

While the above explanation illustrates who to handle a pre-existing data set, having calculated the relationship in D=d+1 dimensional data space in step 43, this relationship can then be used in a real time data monitor which is accepting new data points having D=d+1 parameters as illustrated in step 47. For each new data point the provisional novelty index in D=d+1 dimensions is calculated in step 48, the probability value read off the curve generated in step 43 and used to find the corresponding novelty index for D-dimensions in step 45.

Detecting Sensor Malfunction

The inventive concepts is also applicable to allow the detection of sensor malfunction in multi-parameter monitoring devices. The term "sensor malfunction" as used here does not just mean malfunction of the sensing device itself, but also situations where the sensor may have fallen off or where there may be a connection problem between the sensor and the monitoring device.

The way the present invention allows detection of such sensor malfunction is to compare the novelty-index-based probability value for the current state of the system as represented by all sensor inputs, with the probability values calculated by ignoring (in turn) individual ones of the sensor inputs. If the probability value calculated by ignoring, say, the $m^{th}$ sensor is much higher (more normal) than the probability value calculated by using all sensor inputs then it is likely that there is a problem with that single $m^{th}$ sensor. This is based on the assumption that a genuinely abnormal state of the system being monitored would tend be reflected by abnormal values in more than one sensor.

Figure 5:
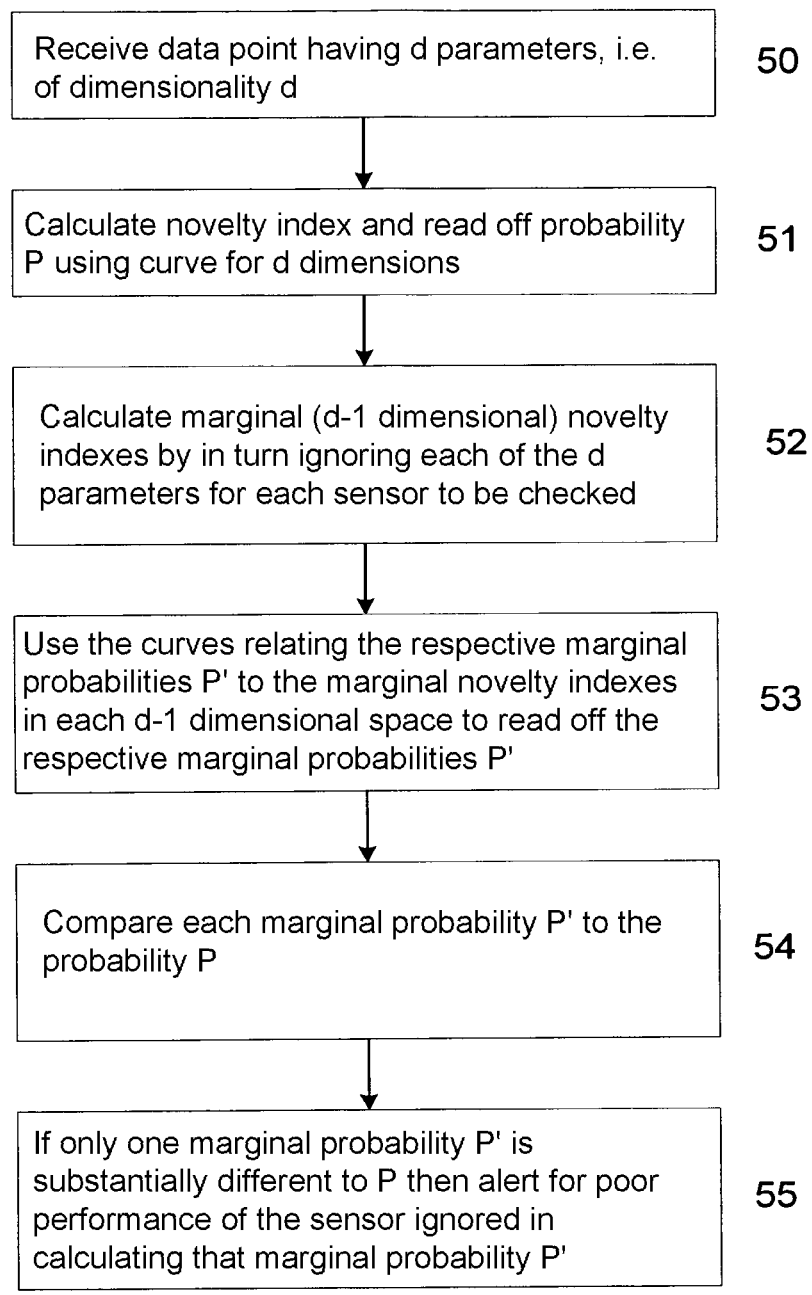
FIG. 5 is a flow diagram explaining an embodiment of the invention which detects sensor malfunction.

FIG. 5 illustrates the process flow. This process is executed by the processor one of the apparatus illustrated in FIG. 1.

Step 50 illustrates reception of a data point having d parameters, one from each of d sensors. In step 51 the novelty index is calculated using Equations (1) and (2) and then the corresponding probability value is found using the relationship in d-dimensions between novelty index and probability value such as that illustrated in FIG. 7 (which is for 5 dimensions). This gives a probability value $P_d$ based on the full 5-dimensional data point.

In step 52 marginal novelty indexes are calculated in turn by ignoring a different one of the d parameters of the data point. Thus for a data point of originally 5-dimensions there will be five different marginal novelty indexes calculated, one for each of the different 4-dimensional spaces. In step 53 the marginal probabilities $P'_{d-1}$ are obtained from the relationship between marginal probability and marginal novelty index such as those shown in FIG. 6(B). Thus for each data point five different marginal probabilities are obtained, each one corresponding to the probability value ignoring a different one of the parameters.

In step 54 each of the marginal probability values $P'_{d-1}$ are compared to the probability value $P_d$ calculated for all d parameters. Then, as illustrated in step 55, if there is a significant disparity (i.e. the magnitude of the difference is greater than a predetermined threshold) between only one of the marginal probability values and the full d-dimensional probability value $P_d$ then an alert for poor performance of the sensor whose parameter is ignored for that marginal probability value is generated.

The invention claimed is:

1. A method of determining and displaying an index of novelty representing the state of a system based on measurements of a plurality of different parameters of the system, the system being a physical system or a biological system, the plurality of parameters defining respective dimensions of a multi-dimensional measurement space, the method being performed by a processor, and the method comprising the steps of:
receiving sets of values each value in a set being a measurement of a different one of said plurality of parameters, each set defining a data point in said multi-dimensional measurement space;
calculating the index of novelty for each data point by comparing the position in said multi-dimensional measurement space of each data point to a set of prototype data points comprising measurements of said parameters representative of the system being in a normal state,
wherein in the event of receipt of a deficient data point missing one or more of said parameter values of said set, the method further comprises the steps of:
calculating a marginal index of novelty of the deficient data point based on the position of the deficient data point in a reduced dimensionality space omitting the dimensions corresponding to the missing parameter values,
using a predefined relationship, calculated for said reduced dimensionality space, between the marginal index of novelty and the marginal probability of different states of the system to find a marginal probability value representing the probability of the system being at least as close to said normal state as the state represented by the deficient data point,
using a further predefined relationship, calculated for said multi-dimensional measurement space, between the index of novelty and the probability of different states of the system to find the index of novelty in said multi-dimensional measurement space corresponding to a probability equal to said marginal probability value; and
displaying the index of novelty so found as the index of novelty for the deficient data point.

2. A method according to claim 1 wherein the marginal index of novelty of the deficient data point is based on comparing the distance of the deficient data point in the reduced dimensionality space from a set of prototype data points comprising measurements of said parameters representative of the system being in a normal state.

3. A method according to claim 2 wherein the set of prototype data points in the reduced dimensionality space are the prototype points in the multi-dimensional measurement space omitting the dimensions corresponding to the missing parameter values.

4. A method according to claim 1 wherein in calculating the index, or marginal index, of novelty for each data point its position is compared to the set of prototype data points using a probability density function based on the Euclidian distance between that data point and each of the prototype data points.

5. A method according to claim 4 wherein the probability density function is the Parzen Windows function.

6. A method according to claim 1 wherein the prototype points are cluster centres in a training set of multiple samples of data points.

7. A method according to claim 6 wherein the same cluster centres are used in calculating the marginal index of novelty in the reduced dimensionality space regardless of which parameter values are missing.

8. A method according to claim 6 wherein the cluster centres are recalculated in each reduced dimensionality space.

9. A method according to claim 1 wherein the predefined relationships in said reduced dimensionality space and in said multi-dimensional measurement space are based on a training set of multiple samples of data points.

10. A method according to claim 9 wherein the predefined relationships are based on taking as thresholds values of the index, or marginal index, of novelty progressively ranging from a minimum to a maximum value, finding for each of said thresholds the fraction of data points in the training set which have an index, or respectively marginal index, of novelty below the threshold, and taking that fraction as the probability value, or respectively marginal probability value, for that index, or respectively marginal index, of novelty.

11. A method according to claim 1 wherein a plurality of the predefined relationships in different reduced dimensionality spaces are used, each being based on the same single training set of data points and omitting a different parameter or combination of parameters from the sets of values forming each data point of the training set.

12. An apparatus for determining and displaying an index of novelty representing the state of a system based on measurements of a plurality of different parameters of the system, the apparatus comprising the processor performing the method of claim 1, an input for receiving said measurements of a plurality of different parameters, and a display for displaying the index of novelty.

13. A method of determining and displaying an index of novelty representing the state of a system based on measurement of a plurality of different parameters of the system, the system being a physical system or a biological system, the method being performed by a processor, and the method comprising the steps of:
receiving a data set comprising a plurality of sets of values each value being a measurement of a different one of said plurality of parameters, each set of values defining a data point in measurement space of dimension D, where D is a positive integer greater than one;
calculating a provisional index of novelty for each data point by comparing the position in said measurement space of dimension D of each data point to a set of prototype data points comprising measurements of said parameters representative of the system being in a normal state;
calculating a relationship, in said measurement space of dimension D, between the provisional index of novelty and the probability of different states of the system to find a probability value representing the probability of the system being at least as close to said normal state as the state represented by a data point having that provisional index of novelty, using said calculated relationship to find for each data point of the data set the probability value corresponding to its provisional index of novelty;

using a further predefined relationship between the probability of different states of the system and an index of novelty defined in a space of dimension L, where L is a positive integer less than D, and based on comparing the distance between a data point and said normal state of the system, to find for each data point of the data set the index of novelty corresponding in the space of dimension L to said probability value; and displaying the index of novelty so found as the index of novelty for that data point.

14. A method according to claim 13 wherein in calculating the index, or provisional index, of novelty for each data point its position is compared to the set of prototype data points using a probability density function based on the Euclidian distance between that data point and each of the prototype data points.

15. A method according to claim 14 wherein the probability density function is the Parzen Windows function.

16. A method according to claim 13 wherein the predefined relationships are based on taking as thresholds values of the index, or provisional index, of novelty progressively ranging from a minimum to a maximum value, finding for each of said thresholds the fraction of data points which have an index, or respectively provisional index, of novelty below the threshold, and taking that fraction as the probability value for that index, or respectively provisional index, of novelty.

17. An apparatus for determining and displaying an index of novelty representing the state of a system based on measurements of a plurality of different parameters of the system, the apparatus comprising the processor performing the method of claim 13, an input for receiving said measurements of a plurality of different parameters, and a display for displaying the index of novelty.

18. A method of detecting sensor malfunction amongst a plurality of different sensors each measuring a parameter of the system, the plurality of parameters defining respective dimensions of a D-dimensional measurement space, where D is equal to the number of sensors, the method comprising the steps of:

receiving sets of values, each value in a set being a measurement from a different one of said sensors, each set defining a data point in said D-dimensional measurement space;

calculating an index of novelty for each data point by comparing its position in said D-dimensional measurement space to a set of prototype data points comprising measurements of said parameters representative of the system being in a normal state;

using a predefined relationship, calculated for said D-dimensional measurement space, between the index of novelty and the probability of different states of the system to find a probability value representing the probability of the system being at least as close to said normal state as the state represented by the data point;

calculating for each data point at least one marginal novelty index by ignoring one parameter value from said set of values and comparing the position of the data point in a D-1 dimensional space to the set of prototype data points also in the D-1 dimensional space, the D-1 dimensional space omitting the dimension corresponding to the ignored parameter;

using a further predefined relationship, calculated for said D-1 dimensional space, between the marginal index of novelty and the marginal probability of different states of the system to find a marginal probability value representing the probability of the system being at least as close to said normal state as the state represented by the marginal novelty index;

comparing said probability value and said marginal probability value; and in the event of the probability value and marginal probability value differing by more than a predefined threshold, outputting an alert for malfunction of the sensor whose parameter value was ignored.

19. A method according to claim 18 further comprising repeating the steps of calculating a marginal novelty index and finding a marginal probability value for each data point, each time ignoring a different parameter value, and comparing each resulting marginal probability value to the probability value, to check for malfunction of each of said sensors.

20. A method according to claim 18 further comprising outputting the alert if only one marginal probability value differs by more than a predefined threshold from said probability value.

21. A method according to claim 18 wherein in calculating the index, or marginal index, of novelty for each data point its position is compared to the set of prototype data points using a probability density function based on the Euclidian distance between that data point and each of the prototype data points.

22. A method according to claim 21 wherein the probability density function is the Parzen Windows function.

23. A method according to claim 18 wherein the prototype points are cluster centres in a training set of multiple samples of data points.

24. A method according to claim 23 wherein the same cluster centres are used in calculating the marginal index of novelty in the D-1 dimensionality space regardless of which parameter value is missing.

25. A method according to claim 18 wherein the predefined relationships in said D-1 dimensionality space and in said D-dimensional measurement space are based on a training set of multiple samples of data points.

26. A method according to claim 25 wherein the predefined relationships are based on taking as thresholds values of the index, or marginal index, of novelty progressively ranging from a minimum to a maximum value, finding for each of said thresholds the fraction of data points in the training set which have an index, or respectively marginal index, of novelty below the threshold, and taking that fraction as the probability value, or respectively marginal probability value, for that index, or respectively marginal index, of novelty.

27. An apparatus for detecting sensor malfunction amongst a plurality of different sensors each measuring a parameter of the system, the apparatus comprising an input for receiving inputs from said sensors, a processor adapted to execute the method steps of claim 18, and a device for outputting said alert.

28. A method according to claim 1 wherein the system is human or animal.

29. A method according to claim 1 wherein the parameters are medical measurements.

30. A method according to claim 29 wherein the parameters comprise any of heart rate, blood pressure, temperature, blood oxygen saturation, breathing rate, Glasgow Coma Score.

* * * * *